United States Patent [19]
Oakley et al.

[11] Patent Number: 4,897,359
[45] Date of Patent: Jan. 30, 1990

[54] APPARATUS FOR OXYGENATING CULTURE MEDIUM

[75] Inventors: Robert V. Oakley, Lafayette; Van Taiariol, Redwood City; Rudolpf F. Bliem, Castro Valley; James F. Long, San Francisco, all of Calif.

[73] Assignee: Bio-Response, Inc., Hayward, Calif.

[21] Appl. No.: 329,013

[22] Filed: Mar. 27, 1989

[51] Int. Cl.⁴ ............................................. C12M 1/04
[52] U.S. Cl. ................................. 435/313; 261/122; 261/124
[58] Field of Search ................ 261/122, 124; 435/313

[56] References Cited

U.S. PATENT DOCUMENTS

| | | | |
|---|---|---|---|
| 3,821,087 | 6/1974 | Knazek et al. | 435/313 |
| 3,997,396 | 12/1976 | Delente | 195/1.8 |
| 4,144,136 | 3/1979 | Corbell | 195/127 |
| 4,583,969 | 4/1986 | Mortensen | 261/122 |
| 4,649,114 | 3/1987 | Miltenburger et al. | 435/240 |
| 4,720,462 | 1/1988 | Rosenson | 435/285 |
| 4,781,889 | 11/1988 | Fukasawa et al. | 422/48 |

Primary Examiner—Carroll B. Dority
Attorney, Agent, or Firm—St. Onge Steward Johnston & Reens

[57] ABSTRACT

An oxygenator, particularly for proving oxygen and/or carbon dioxide or other gases to culture medium used in the in vitro culture of animal cells, comprised of a collection of elongate gas-permeable, liquid-impermeable tubes through which oxygen-containing gas flows and permeates through the tube walls to provide bubble- and foam-free oxygen gas to medium in contact with or in proximity to the tubes, the individual tubes having an outside diameter of less than about 1 mm and a wall thickness of from about 0.1 mm to about 0.25 mm, the tube collection preferably be radially spread apart at at least one point along its length.

11 Claims, 3 Drawing Sheets

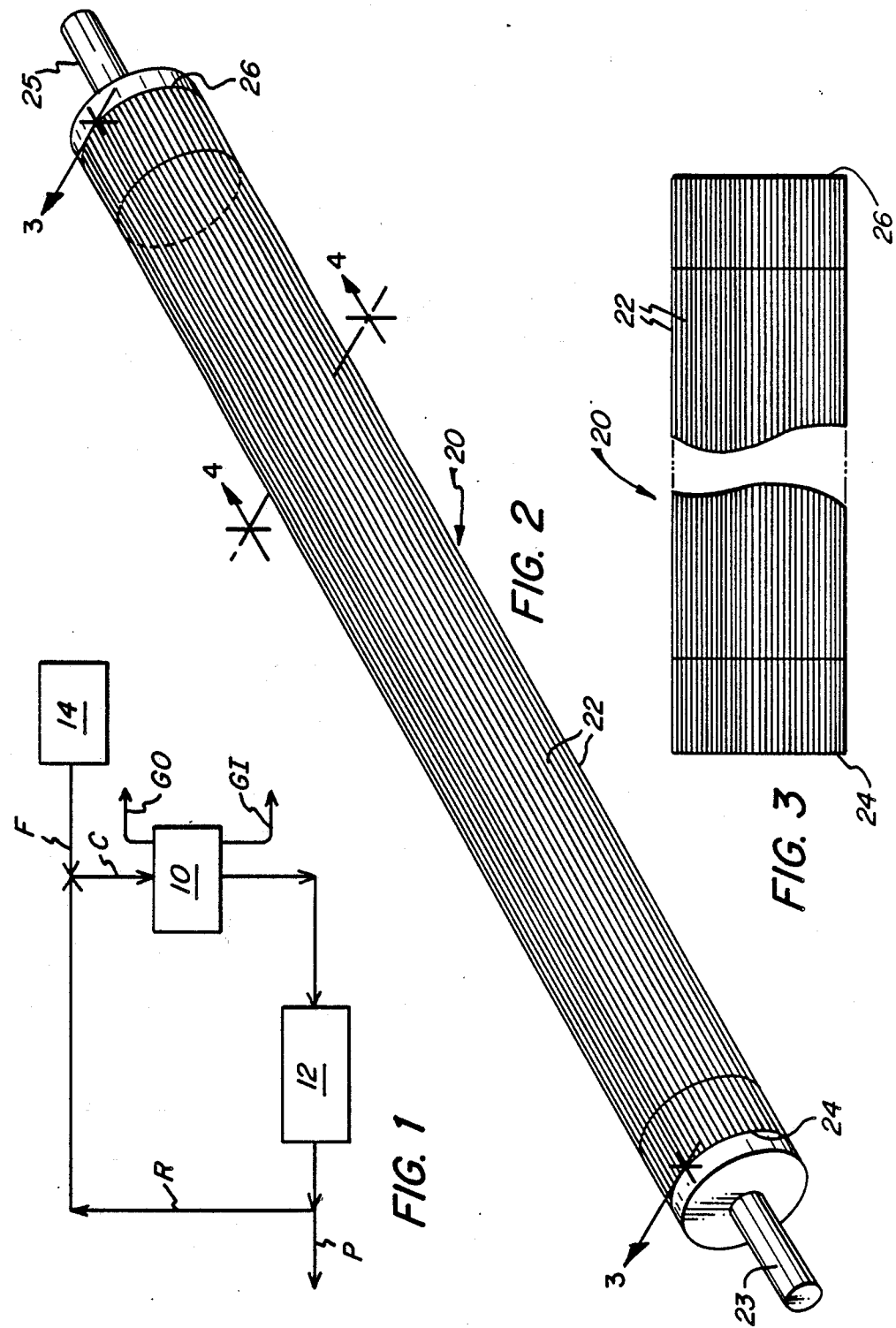

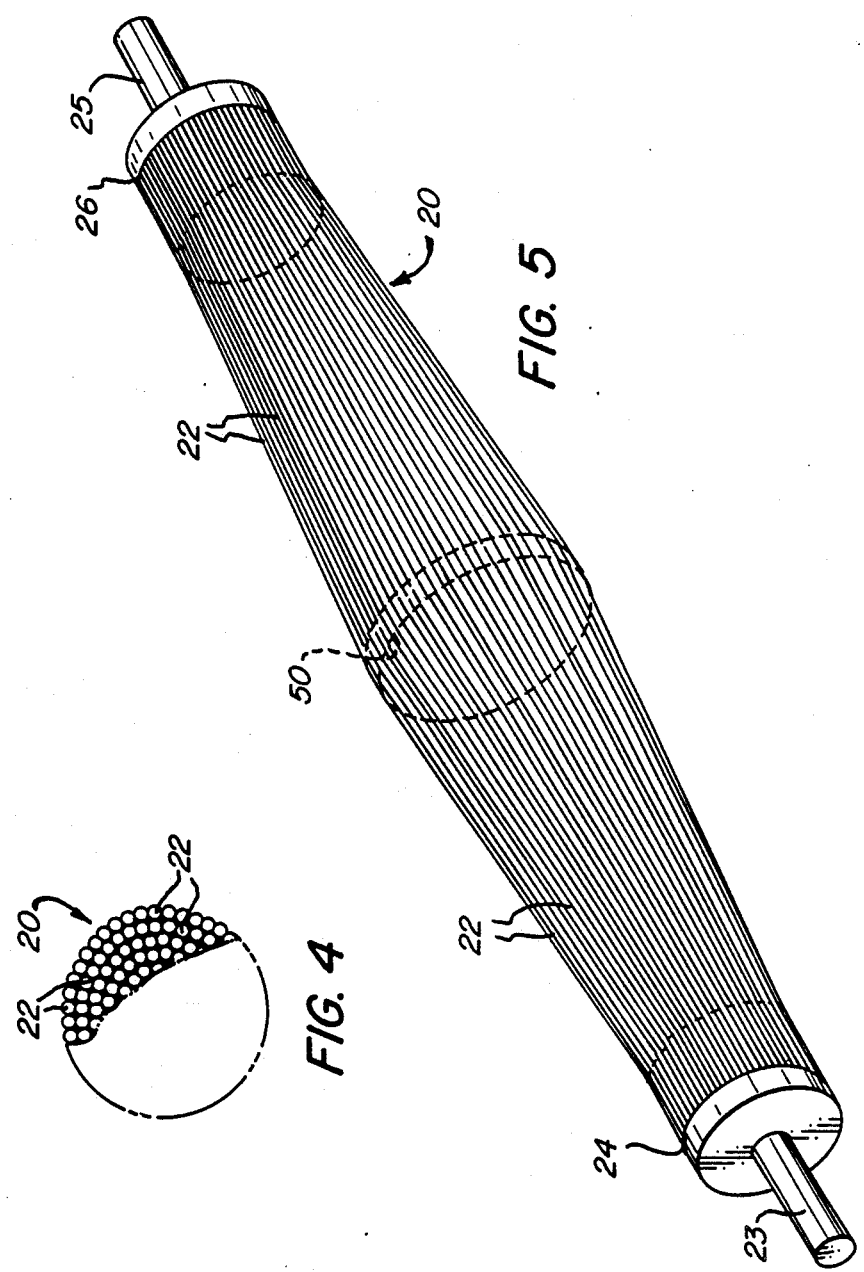

APPARATUS FOR OXYGENATING CULTURE MEDIUM

BACKGROUND OF THE INVENTION

The present invention relates to the in vitro culture of animal cells and, more particularly, to an apparatus for oxygenating culture medium employed in the in vitro culture of animal cells.

The in vitro culture of animal cells, particularly for purposes of recovering proteins either normally secreted by such cells or secreted by such cells by virtue of manipulation of their genetic machinery, has assumed increasingly greater prominence as a consequence of the increasing need for large quantities of proteins for therapeutic, diagnostic and investigative purposes, and the recognition that animal cells (per se, or as a hybrid partner, or as a host for an exogeneous gene) offer the best source of proteins which are the same as or closely similar to those actually employed by animals (e.g., humans) in vivo in carrying out regulatory, immune response, and other like functions.

Despite the recognized advantages of, and needs for, in vitro animal cell culture, the culture of cells outside the animal body is a difficult proposition at best, made even more difficult by the present-day demand that such processes be carried out efficiently and economically so as to achieve ultimate protein products which are not unreasonably expensive. The ultimate aim of in vitro animal cell culture processes is to provide the cells with an environment which closely mimics that which the cells are exposed to in vivo, in terms, e.g., of nutritional requirements, oxygen requirements, temperature, pH, carrying away of wastes, etc., thereby permitting the cells to grow, behave and produce product as they would in vivo, with the added burden of attempting to mimic this environment in larger scale than the microenvironment which normally would be present, for these cells, in the animal itself. At least in theory, it is possible to devise elaborate in vitro systems involving simulations of capillaries, lungs, kidneys and the like to provide the requisite environment, but often not in any remotely cost-effective manner.

A great many in vitro animal cell culture devices and systems are known in the art for culture of both anchorage-dependent cells and cells which can be grown without need for attachment to a substrate. These devices and systems run the gamut from small-scale flasks or roller bottles to somewhat larger scale hollow-fiber reactors, stirred tank reactors, packed bed reactors, and the like. In each, the cells are bathed or submerged in a liquid culture medium which provides the cells with essential nutrients for growth and maintenance and into which the cells secrete products, including protein products of interest.

Among the most important "nutrients" for animal cells is oxygen, and the provision of means for supplying the required degree of oxygen to the culturing cells not only is among the most difficult aspects of cell culturing, but may indeed act to restrict or dictate choice among otherwise potentially available cell culture devices or systems and their scale of feasible operation.

One means for supplying oxygen to cells in culture is by means of surface aeration, i.e., providing oxygen or oxygen-containing gas in the headspace, above the culture medium level, in a closed culture system. Generally, however, the rate at which oxygen can diffusively transfer from the gas phase to the liquid phase in such systems is relatively low and, thus, growth and maintenance of only a relatively small number of cells can be supported in this manner, relegating it to utility only in small flasks or vessels. The rate of gas transfer can be increased if the liquid phase is agitated (e.g., as in a stirred reactor), but here again the increase is not so great as to offer utility in anything other than relatively small systems.

Another means for providing oxygen to cells in culture medium is to bubble gas directly through the culture (sparging). While this is a very efficient means of oxygenation, it generally is very damaging to animal cells. Also, sparging leads to foam formation which itself can damage the cells. Although the use of surfactants can eliminate or suppress foam formation, the presence of the surfactant in the eventually harvested culture medium can lead to very difficult and expensive problems in purification of the desired secreted protein product.

It also has been proposed to provide oxygen to cells submerged in culture medium (e.g., as in a stirred-tank reactor) by indirect sparging, i.e., passing oxygen into or on one side of a gas-permeable (but generally liquid-impermeable) tube or membrane arranged in the medium (e.g., silicone rubber tubes or sheets), and through or across which the oxygen permeates into the culture medium. It is generally possible in this way to achieve bubble-free and foam-free aeration, although gassing efficiency is not as high as in direct sparging.

Another means for providing oxygen to cells is to continuously or intermittently remove culture medium from the system, separately gasify the medium to provide it with oxygen, and then return the medium to the cell culture system where it can give up its oxygen to the cells. Although somewhat inherently limited by the relatively low solubility of oxygen in the culture medium, operation in this manner can prove quite effective, and is often employed in association with cell culture devices (e.g., packed-bed reactors, hollow fiber reactors, fluidized bed reactors and the like) which are designed to retain cells therein while culture medium is removed for oxygenation and recirculated to the reactor. While closed loop systems of this type are operable at free cell suspension densities (i.e., the density of cells not retained in the reactor when medium is withdrawn therefrom) which are significantly lower than is the case with stirred reactors, the removed medium nevertheless generally contains a number of cells which is still sufficiently large to bring about concern for damage to these cells during oxygenation of the medium.

Along these lines, it is known to employ blood oxygenators or other artificial lung-type devices to provide oxygen to culture medium removed (along with a fair number of cells) from a culture device, wherein the oxygen is provided to the medium across gas-permeable, liquid-impermeable membrane surfaces (e.g., in the form of tubes, hollow fibers or sheets), but the devices known heretofore for such purpose prove quite inefficient and/or troublesome, particularly when large-scale, cost-effective culture is at issue. For example, in order to provide oxygenation of the culture medium sufficient to support large-scale culture of cells it is desirable that the rate of mass transfer of gas across the membrane and into the culture medium be as large as possible, and that the available surface area over which mass transfer takes place also be large. At the same time, it is necessary that the oxygenation apparatus be capable of withstanding the rigors of continuous, long-term operation, requiring that the materials be capable of repeated autoclaving or like sterilization cycles and that the apparatus not too easily or readily clog with cells and cell debris contained in the culture medium. These desires and concerns are often self-contradictory, leading to compromise constructions which, e.g., provide large surface areas and thin membranes to optimize mass transfer, but which break down (leading to bubble and foam formation) after more than a single sterilizing cycle; or provide hearty membrane surfaces for strength but have poor mass transfer characteristics and need to be made very large; or provide reasonably-sized yet tightly packed or wound membrane surfaces which readily foul and/or limit medium throughput and/or cause the medium to seek out preferential flow pats therethrough and thus reduce the effective area of gas transfer. As a consequence, none of the constructions and configurations permit of the long-term, cost-effective, efficient oxygenation demanded for commercial-scale in vitro cell culture.

SUMMARY OF THE INVENTION

It is the primary object of this invention to provide an apparatus for oxygenating culture medium, including cell-containing culture medium, so as to provide cells in contact with this medium with the required degree of oxygen to support growth and maintenance of a large number of culturing cells, particularly for use in conjunction with closed loop systems in which the culture medium is passed through the cell culture reactor, oxygenated separate from the cell culture reactor, and then recirculated thereto, and most particularly for use in association with cell culture reactors of the packed bed, fluidized bed, hollow fiber, or the like type, designed to largely retain cells therein as culture medium is removed for oxygenation.

Another object of the present invention is to provide an apparatus of the type described which achieves efficient oxygenation with minimum fouling, but which at the same time can withstand the rigors of repeated sterilization.

Yet another object of the invention is to provide an oxygenation apparatus which can be scaled-up to larger scale operation and which can easily be removed from the overall culture system for regeneration, resterilization and eventual reuse.

These and other objects are achieved by the provision of an oxygenation apparatus comprised of a plurality of elongated, thin, generally cylindrical, hollow tubes, disposed substantially in parallel, the walls of which tubes are composed of gas-permeable, liquid-impermeable material, one entry end of such tubes being arranged in a substantially common plane and adapted to receive gas into the bores of the tubes, and the other end of such tubes being arranged in a substantially common plane and adapted for withdrawal of gas passing through the bores of said tubes, and wherein substantially all the hollow tubes have an outside diameter of less than about one millimeter and a wall thickness of from about 0.1 to about 0.25 millimeters.

In the preferred embodiment of the invention, the assembly of elongated substantially parallel hollow tubes is radially spread apart at at least one location along its length to provide for increased spacing among the tubes.

In accordance with the invention, the assembly of gas-permeable, liquid-impermeable elongate hollow tubes, by virtue of their small individual size (i.e., less than about 1 mm O.D.) and relatively thin walls (i.e., less than about 0.25 mm) presents a large surface area per unit tube assembly volume (and/or per unit liquid passing in contact with the tubes), thus enabling provision of efficient oxygenation without need for larger cumbersome unit sizes. At the same time, the wall thickness is sufficiently large (i.e., at least about 0.1 mm) to provide sufficient strength in each tube to operate satisfactorily in production-scale processes, to provide a sufficiently small bore to enable use of high gas pressures through the tubes (e.g., up to about 25 psia), and to withstand numerous regeneration/resterilization cycles. The configuration of the unit permits it to be readily removed or isolated from the overall culture system for regeneration/resterilization. The units also lend themselves to easy fabrication from multiple lengths of tubing.

As a consequence of the foregoing features, high rates of mass transfer are achieved by reason of the thin gas-permeable walls across which the gas passes, the high gas pressure capabilities of the small bore tubing, and the high liquid velocity capabilities of the construction without fouling or channeling, with such mass transfer occurring over a large membrane surface area with which the culture medium is effectively in contact. Because the tube walls are yet sufficiently robust and because the apparatus does not involve adhesively-bound multi-layer laminates of membrane materials, the apparatus is capable of long-term use in production culture systems, including repeated autoclaving or other like sterilization cycles. These advantages are still further augmented in the preferred construction, since the spread-apart tubes permit of reduced fouling tendencies, and encourage a more transverse, turbulent flow of culture medium across the gas-permeable membrane surfaces thus improving mass transfer and sweeping of cells off membrane surfaces. By reason of the simple geometric configuration in all embodiments, the parameters of liquid velocity, gas transfer rates, and the like for unit lengths, areas and the like lend themselves to relatively precise calculation and, thus, relatively predictable scale-up.

The typical use of the oxygenator of the present invention is in separately oxygenating a culture medium which will then be introduced (or re-introduced) into a culture system where the cells then receive all or a part of their oxygen requirements from the oxygen dissolved in the oxygenated medium. The fact that such medium will not be completely cell-free (and indeed may contain a relatively large number of cells) is not problematic since the oxygenation of the medium is performed in a way (i.e., across a gas-permeable tube wall surface) which minimizes cell damage, and since the unit configuration largely prevents fouling. Alternatively, however, the oxygenation apparatus can be used as a means for providing oxygen directly to a culture of medium and cells (e.g., submerging the apparatus in the medium in a stirred-tank reactor), although its effectiveness in such situations may be limited due to the inability to achieve a desirably high gas transfer surface to liquid volume without extensive design modifications. Of course, it is possible to employ the oxygenation apparatus in any situation where provision of oxygen to a liquid medium (e.g., blood) is desired.

It will also be understood that the apparatus of the present invention is generally effective for providing any gas to a liquid, and in the specific context of cell culture, can be used not only to provide oxygen to a culture medium, but also for providing other gaseous components thereto, such as carbon dioxide, either with oxygen or alone for brief period, to alter and/or regulate the pH of the medium as is conventional in the art.

BRIEF DESCRIPTION OF THE DRAWINGS

FIG. 1 is a schematic of an in vitro animal cell culture system in which the oxygenation apparatus of the present invention can be employed.

FIG. 2 is a perspective view of one embodiment of the oxygenation apparatus of the invention.

FIG. 3 is a cross-sectional view of the apparatus of FIG. 2 through line 3—3.

FIG. 4 is a cross-sectional view of the apparatus of FIG. 2 through line 4—4.

FIG. 5 is a perspective view of an oxygenation apparatus according to the preferred embodiment of the invention.

DETAILED DESCRIPTION OF THE INVENTION

Figure 6:
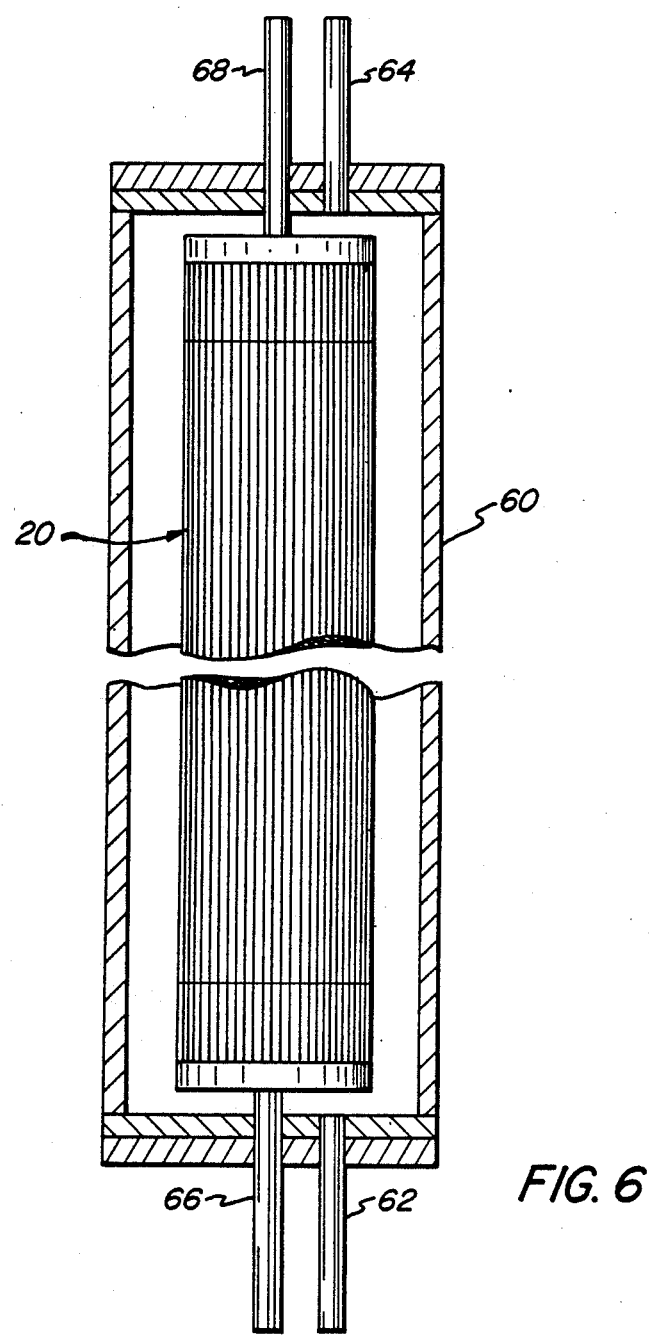
FIG. 6 is a cross-sectional view of an oxygenation apparatus according to the invention contained in a housing through which culture medium is flowed.

As set forth generally in FIG. 1, a typical in vitro animal cell culture unit in which the oxygenation apparatus of the present invention will find use is a closed-loop system in which cells contained in bioreactor 12 are bathed with oxygenated culture medium which is continuously or intermittently fed to and withdrawn from the bioreactor 12. A portion (P) of the effluent stream of spent culture fluid is removed for further processing to recover protein product therefrom, while the remaining portion (R) is recycled, mixed with fresh culture medium (F) from supply source 14, and the commingled medium (C) then oxygenated at oxygenator station 10 before reentry into the bioreactor 12, oxygenator station 10 being provided with gas inlet (GI) and gas outlet (GO) lines for providing gas to the medium passing therethrough. Typically, the system will have associated with it a variety of monitors, sensors and controls for monitoring and regulating culture medium flows, oxygen content, pH and other like parameters.

In the schematic shown in FIG. 1, the oxygenation apparatus according to the present invention is arranged within the oxygenation station 10, which will comprise a fluid tight housing having inlet and outlet ports for receipt and withdrawal of culture medium; the oxygenation apparatus which will provide gas to the incoming medium; and inlet and outlet ports for providing gas to and withdrawing gas from the oxygenation apparatus.

One form of the oxygenation apparatus per se (designated as 20) is shown in perspective in FIG. 2. The apparatus contains a plurality of individual elongated thin generally cylindrical hollow tubes 22 which are gas permeable but essentially liquid impermeable. The hollow tubes are generally arranged in parallel and in relatively tightly-packed configuration, preferably in the form of an elongate cylinder. The respective ends of the hollow tubes are joined in common planes to form gas inlet and gas outlet faces 24 and 26 which are in communication with gas inlet tube 23 and gas outlet tube 25, respectively. Oxygen or oxygen-containing gas flowed through gas inlet tube 23 distributes across the inlet hollow tube face 24 and causes gas to flow through the bores of the hollow gas-permeable tubes 22. To the extent gas flowing through the bores of the hollow gas-permeable tubes 22 does not completely permeate through the walls of the tubes, it continues through the tube bores for exit at outlet face 26 and outlet gas tube 25.

Critical to attainment of the advantages of the present invention is the utilization of gas-permeable, liquid-impermeable hollow tubes 22 which possess defined characteristics of overall thickness (or diameter) and wall thickness, and these in turn, of course, defining characteristics of the size of the tube bore, i.e., its inner diameter. In particular, silicone rubber tubing is the preferred material of construction, and the tube outer diameter is less than about 1 mm (and generally greater than about 0.6 mm), while the tube wall thickness is from about 0.1 mm to about 0.25 mm, and preferably from about 0.2 mm to about 0.25 mm. With hollow tubes of this small size, it is possible to provide a large number of such tubes in a reasonable overall volume, hence, a large gas/liquid contact surface area, while still permitting relatively high liquid velocities through the unit and minimum clogging or fouling; to provide walls which are sufficiently thin to enhance the rate of mass transfer of gas therethrough yet sturdy enough to withstand production-scale operation and numerous cycles of regeneration/resterilization without significant material degradation; and to provide sufficiently small bores (e.g., less than about 0.5 mm) to permit high pressure gas throughput, thus further enhancing the rate of gas transfer.

By way of example, utilizing about 700 individual lengths of silicone rubber tubes having an O.D. of about 0.96 mm, an I.D. of about 0.50 mm, and a wall thickness of about 0.23 mm, an oxygenator can be constructed in generally elongate cylindrical form having an overall length of about 30 inches and a diameter of about 1.375 inches, presenting a gas exchange surface area of about 13,935 $cm^2$, capable of operation at gas pressures up to about 25 psia, and which is not significantly degraded after three autoclave sterilizations.

For constructing the oxygenator apparatus of FIG. 2, lengths of the silicone rubber tubing are collected together and the respective ends (e.g, about 1–2 inches from each side) then potted with suitable adhesive in known manner to produce end faces at either end of the unit terminating in open bores through which gas can flow into the tubes and be withdrawn from the tubes (to the extent all the gas entering the tubes does not permeate radially and through the gas-permeable tube walls). Obviously, either end of the unit can be chosen as the gas inlet or gas outlet end.

The oxygenator of FIG. 2 is further illustrated in the sectional views of FIG. 3 and FIG. 4. Thus, as shown in the longitudinal section of FIG. 3, the hollow gas-permeable tubes 22 are arranged generally in parallel and potted at their respective ends to form end faces 24 and 26. Seen in the cross-section of FIG. 4, the hollow gas-permeable tubes 22 are generally quite closely packed so as to provide as much surface area as possible within the overall volume of the unit.

In use, the oxygenator 20 generally will be arranged in a liquid-tight housing 60 (see FIG. 6) through which culture medium to be oxygenated is admitted and withdrawn through suitable liquid inlet and outlet ports 62 and 64, with gas provided to the oxygenator 20 via gas inlet and outlet ports 66 and 68. Generally speaking, the housing should be dimensioned sufficiently larger than the dimensions of the oxygenator so as to permit culture medium to freely flow in contact with the oxygenator, while on the other hand not being so much larger that medium might possibly pass through the housing without being sufficiently proximate the oxygenator to receive oxygen therefrom.

As is apparent, the elongate thin hollow tubes of the oxygenator, particularly when made of silicone rubber, will be generally quite flexible. It is preferred that the oxygenator, in use, be arranged such that the hollow tubes are generally extended to their full length, a result easily achieved either through gravity alone (arranging the oxygenator vertically from a top support) or through other suitable position fixing means.

The inherent flexibility of the hollow gas-permeable tubes generally is sufficient to permit culture medium to flow around and between adjacent tubes even though they are in closely-packed arrangement and to permit the full gassing surface area of the tube collection to efficiently deliver gas to medium flowing around and between the tubes or in close proximity to the oxygenator per se. This is true even when medium containing cells or cell debris is to be oxygenated, since the thin tubes and their flexibility tend to prevent cell adhesion and fouling of tube surfaces.

In the preferred embodiment of this invention, illustrated in the perspective view of FIG. 5, spacer means are included to effect lateral separation among the tubes, which remain substantially parallel thereby increasing their ability to efficiently deliver oxygen through their gas-permeable walls and decreasing the tendency of any fouling by reason of cells or cell debris in the culture medium. Thus, for example, internal spacer element 50 (or multiple spacers) can be arranged at an appropriate point or points along the length of the hollow tube collection so that all tubes 22 are spread apart by passing over the outer periphery of the spacer element to expose more area between adjacent tubes. With construction in this manner, relatively high liquid velocities are possible without channelling, and the liquid flow tends to have a component more transverse to the tubes than is achieved in the strictly longitudinal orientation of FIGS. 2, 3, 4 and 6, all of which enhances gas transfer and minimizes fouling by virtue of the more efficient sweeping of the tube surfaces. Also by reason of the construction, the tendency of cells and cell debris to collect at the respective ends of the tube bundle (i.e., where they are potted together and where little tube flexibility is present and where crevices or pits may exist) is minimized by the slight spreading apart of the tubes at these areas in response to a mid-span spacer.

The key feature of the present invention is the ability to achieve significant transfer of oxygen (or other gas) to the liquid in a reasonably-sized apparatus, without significant detrimental channelling or fouling, in a construction having sufficiently non-complex geometry and operating characteristics to permit of relatively predictable scale-up (in size per se or by adjustment of gas and/or liquid flows), and in a construction which is capable of long-term operation, including repeated sterilization cycles. These features and characteristics make the apparatus ideally suited for large-scale cultivation of animal cells where support of large cell densities are required. By way of example, for the previously described device having a specific surface area of about 7 cm$^{-1}$ (i.e., an available transfer surface of 13935 cm$^2$ and a volume of 2000 cm$^3$), an air flow of 30.9 cm/sec., a liquid flow of 13.3 cm/sec. and a desired oxygenation of the liquid to about 50% saturation, will result in an area specific mass transfer coefficient of 0.1 cm/min. and a mass transfer rate of 0.20 mmol of oxygen/min/liter, and at such rates, the culture of cells at cell densities of $6 \times 10^7$ cells/ml. can be supported by this single oxygenator.

In the preceding description, each of the hollow gas-permeable tubes is described as having particular characteristics regarding outside diameter and wall thickness, and it is indeed preferred that all such tubes which make up the oxygenator possess those characteristics so as to produce an oxygenator which has a large gassing area per unit volume, but which nevertheless is structurally strong enough to withstand production-scale operation and repeated sterilization. It is within the scope of the invention, however, to construct the oxygenator such that substantially all its tubes possess these critical characteristics, while a number of other tubes having different characteristics are also included in the collection.

As previously noted, the preferred use of the oxygenator of the present invention is for the oxygenation of culture medium (including culture medium containing cells and/or cell debris) apart from the culture unit per se. The oxygenator may also be employed, however, within a culture unit containing cells and medium (e.g., as in a stirred-tank reactor) for continuously or intermittently providing oxygen to the cells and medium by means of gas inlet and gas outlet ports arranged in the reactor walls or through a top plate, although as previously noted use in this manner likely will require design modifications to achieve the necessary high ratio of gas transfer surface to liquid volume. Also, of course, the oxygenator is useful for oxygenating (or indeed for providing any gas to) liquids other than culture medium.

The oxygenator of the present invention, in use, e.g., as described in FIGS. 1 and 6, can be scaled-up to any desired size which can be accommodated and/or can be multiply employed in parallel or in series, within a single housing or separate housings, to provide the oxygenation needed for particular quantities of culture medium and to support the growth of particular quantities of cells. By reason of its construction and configuration, the oxygenator is easily isolated and/or removed from culture medium flow lines for cleaning, regeneration, resterilization and reuse. All materials employed for gas inlets, gas outlets, flow lines, housings, etc. are, of course, chosen to be compatible with cell culture and sterilizable.

The foregoing description is made with reference to particular embodiments, illustrations and figures to aid in understanding of the invention and its advantages. As such, they are not intended as restrictions upon the scope of the invention except as set forth in the appended claims.

What is claimed is:

1. An apparatus for providing gas to a liquid, comprising a closely-packed collection of a plurality of elongate generally cylindrical hollow tubes constructed of gas-permeable, liquid-impermeable material, said tubes arranged substantially in parallel along their length, one open terminal end of said tubes being arranged in a substantially common plane to form an inlet face adapted to receive gas for flow through said tubes, and the other open terminal end of said tubes being arranged in a substantially common plane to form an outlet face through which said gas, upon traverse through said tubes, can be withdrawn, said tubes having an outside diameter of less than about 1 mm, and a wall thickness of from about 0.1 mm to about 0.25 mm.

2. The apparatus according to claim 1 wherein said tubes have a wall thickness of from about 0.20 mm to about 0.25 mm.

3. The apparatus according to claim 1 further including means for delivering said gas to said inlet face and means for withdrawing gas from said outlet face.

4. The apparatus according to claim 1 further comprising an internal spacer element at a point along the length of said collection of tubes for effecting radial spreading of the tubes so as to increase the open area between said tubes.

5. An apparatus for providing oxygen or oxygen-containing gas to a liquid, comprising:
a liquid-tight housing;
arranged in said housing, a vertically-oriented oxygenation apparatus comprised of a closely-packed collection of a plurality of elongate generally cylindrical tubes constructed of oxygenpermeable, liquid-impermeable material, said tubes arranged substantially in parallel along their length, one open terminal end of said tubes being arranged in a substantially common plane to form an inlet face adapted to receive an oxygen-containing gas for flow through said tubes, and the other open terminal end of said tubes being arranged in a substantially common plane to form an outlet face through which said gas, upon traverse through said tubes, can be withdrawn, said tubes having an outside diameter of less than about 1 mm and a wall thickness of from about 0.10 mm to about 0.25 mm;
means for introducing liquid to be oxygenated into said liquid-tight housing;
means for removing oxygenated liquid from said liquid-tight housing;
means, communicating with said inlet face to said oxygenation apparatus, for introducing into said liquid-tight housing and into said hollow tubes an oxygen-containing gas; and
means, communicating with said outlet face of said oxygenation apparatus, for removing gas from said hollow tubes and from said liquid-tight housing.

6. The apparatus according to claim 1 wherein said gas is oxygen and wherein said liquid is a culture medium for use in the in vitro culture of animal cells.

7. The apparatus according to claim 5 wherein said liquid is a culture medium for use in the in vitro culture of animal cells.

8. The apparatus according to claim 5 wherein said oxygenation apparatus further comprises an internal spacer element at a point along the length of said collection of tubes for increasing the open area between said tubes.

9. An apparatus for providing oxygen to a culture medium used to support the growth of animal cells in culture, comprising a plurality of elongate hollow tubes constructed of gas-permeable, liquid-impermeable material, said tubes arranged substantially in parallel along their length, one open terminal end of said tubes being arranged in a substantially common plane to form an inlet face adapted to receive an oxygen-containing gas for flow through said tubes, and the other open terminal end of said tubes being arranged in a substantially common plane to form an outlet face through which said gas, after traverse through said tubes, can be withdrawn, said tubes having an outside diameter of less than about 1 mm and a wall thickness of from about 0.1 mm to about 0.25 mm, and each said tube passing over the outer periphery of at least one spacer element arranged along, and in a plane substantially perpendicular to, the length of said plurality of tubes, such that the cross-sectional diameter of said plurality of elongate tubes at said spacer element is greater than that of said plurality of elongate tubes at said respective terminal open ends of said tubes.

10. The apparatus according to claim 9 wherein said gas-permeable, liquid-impermeable material is silicone rubber.

11. The apparatus according to any of claims 1, 2, 3, 4, 5, 6, 7, 8, 9 or 10 wherein said tubes have an outside diameter of greater than about 0.6 mm, and an internal diameter of less than about 0.5 mm.

* * * * *